United States Patent
Pang

(10) Patent No.: US 12,017,027 B2
(45) Date of Patent: Jun. 25, 2024

(54) FUNCTIONAL DRUG INJECTION MODULE

(71) Applicant: WeTTrust Co., Ltd., Seongnam-si (KR)

(72) Inventor: Ji Hwan Pang, Seoul (KR)

(73) Assignee: WeTTrust Co., Ltd., Seongnam-si (KR)

(*) Notice: Subject to any disclaimer, the term of this patent is extended or adjusted under 35 U.S.C. 154(b) by 155 days.

(21) Appl. No.: 17/692,096

(22) Filed: Mar. 10, 2022

(65) Prior Publication Data

US 2023/0046948 A1    Feb. 16, 2023

(30) Foreign Application Priority Data

Aug. 13, 2021  (KR) .......................... 10-2021-0107140

(51) Int. Cl.
*A61M 31/00*   (2006.01)

(52) U.S. Cl.
CPC .......... *A61M 31/00* (2013.01); *A61M 2209/06* (2013.01)

(58) Field of Classification Search
CPC ...... A61M 5/00; A61M 5/002; A61M 25/002; A61M 31/00; A61M 2209/06
USPC ................................................ 206/364, 365
See application file for complete search history.

(56) References Cited

U.S. PATENT DOCUMENTS

| | | | | |
|---|---|---|---|---|
| 4,237,883 | A * | 12/1980 | Akhavi | A61M 5/32 206/365 |
| 5,615,772 | A * | 4/1997 | Naganuma | A61M 5/002 206/364 |
| 5,765,682 | A * | 6/1998 | Bley | A61M 25/002 206/363 |
| 8,517,996 | B2 * | 8/2013 | Fontana | A61M 31/00 206/229 |
| 10,159,796 | B2 * | 12/2018 | Schiff | A61M 5/31511 |
| 2008/0202961 | A1 * | 8/2008 | Sharp | A61M 5/002 206/364 |
| 2014/0110289 | A1 * | 4/2014 | Geuder | A61M 5/3145 141/2 |

FOREIGN PATENT DOCUMENTS

| KR | 10-2014-0000418 A | 1/2014 |
|---|---|---|
| KR | 10-2019-0062738 A | 6/2019 |
| KR | 10-2089261 B1 | 3/2020 |

* cited by examiner

*Primary Examiner* — Bryon P Gehman
(74) *Attorney, Agent, or Firm* — Revolution IP, PLLC

(57) ABSTRACT

Disclosed is a functional drug injection module including: an injection unit including a body that is elongated, keeps a functional drug therein, has an outlet formed at a front end thereof, and is open at a rear end thereof, and a piston that is inserted in the body through the rear end of the body and discharges the functional drug by longitudinally sliding; a cover unit at least partially formed like a projection, inserted in the outlet, and adjust opening/closing of the outlet by selectively separating; and a sealing unit surrounding the injection unit and the cover unit, having a first crease formed in a longitudinal direction of the injection unit, and separating from the injection unit together with the cover unit by being divided along the first crease by external force.

6 Claims, 5 Drawing Sheets

[FIG. 1]
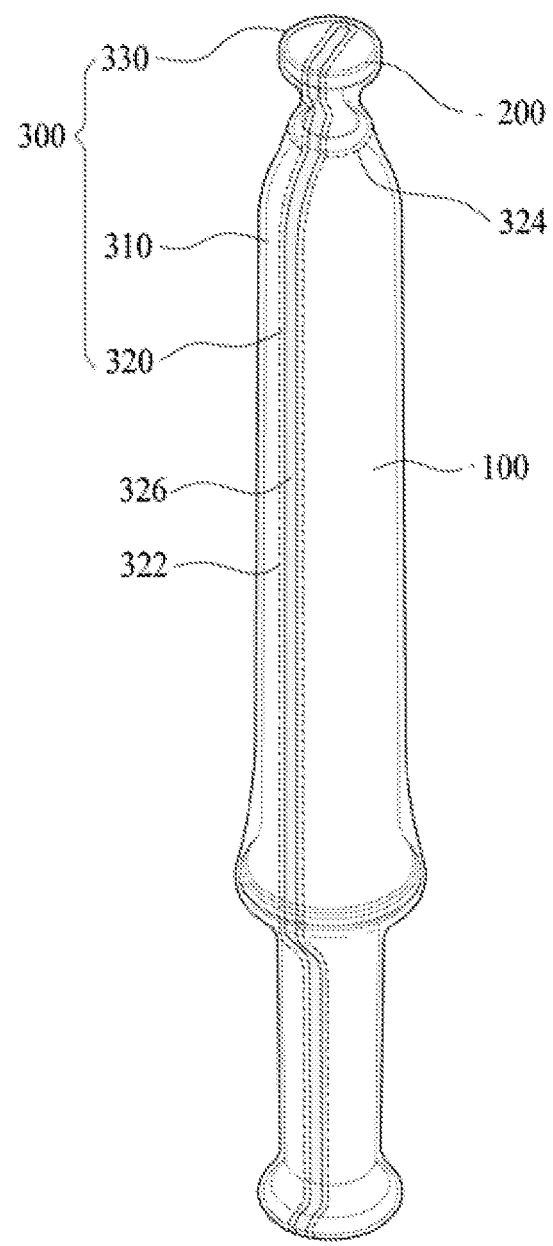

[FIG. 2]
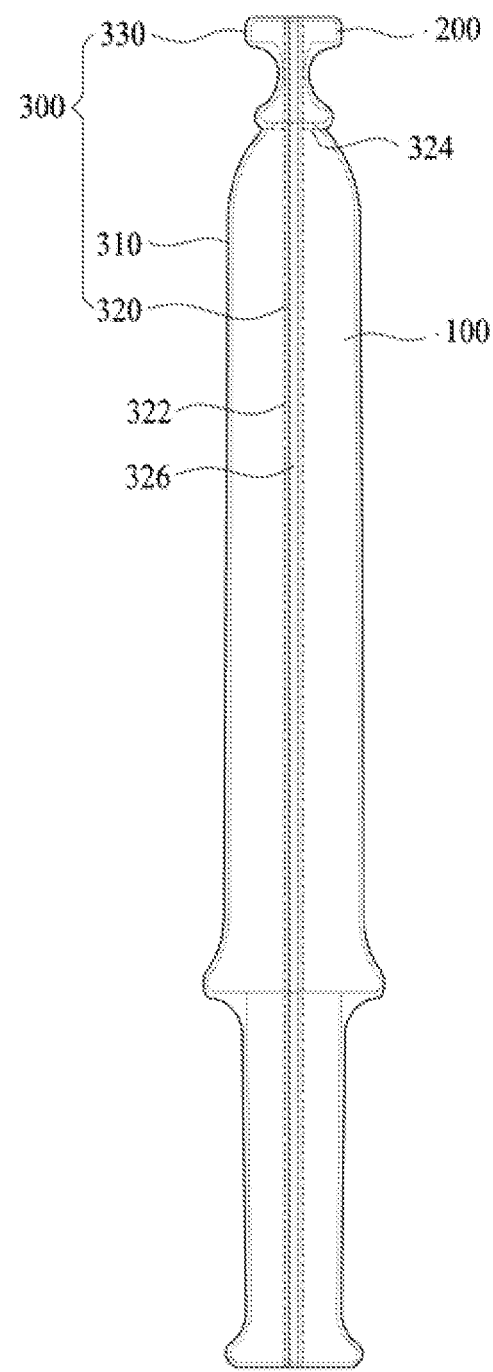

[FIG. 3]
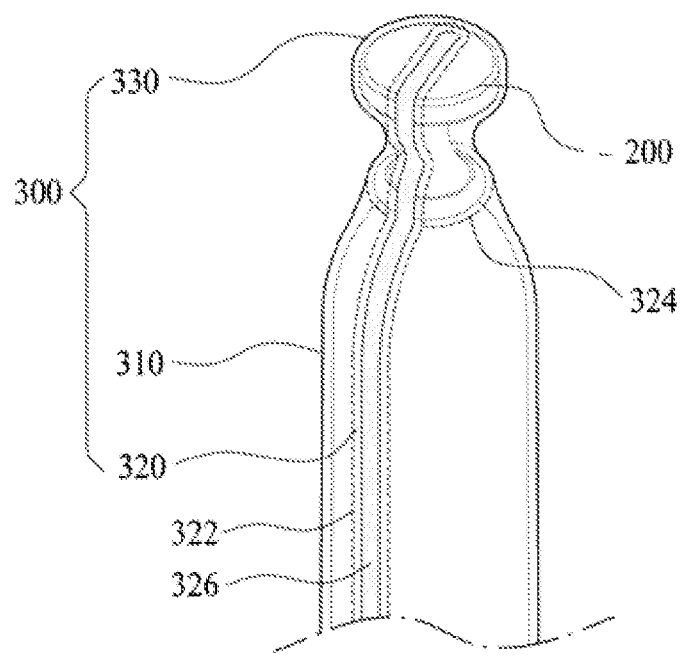
[FIG. 4]
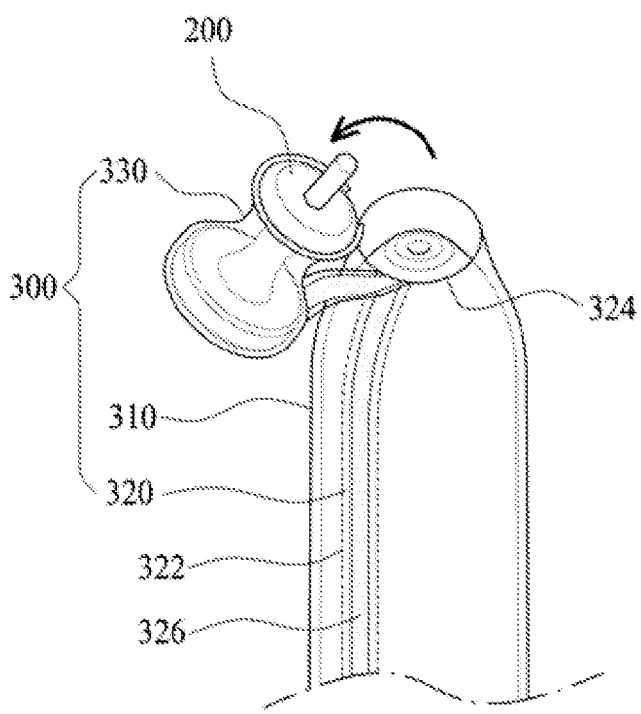

[FIG. 5]
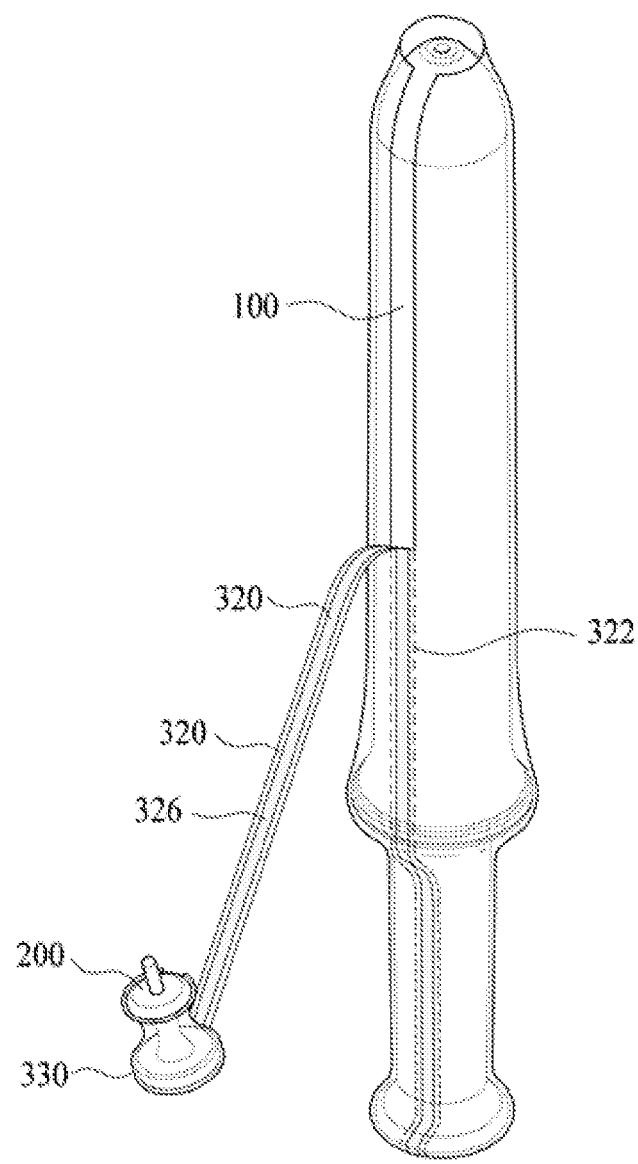

[FIG. 6]
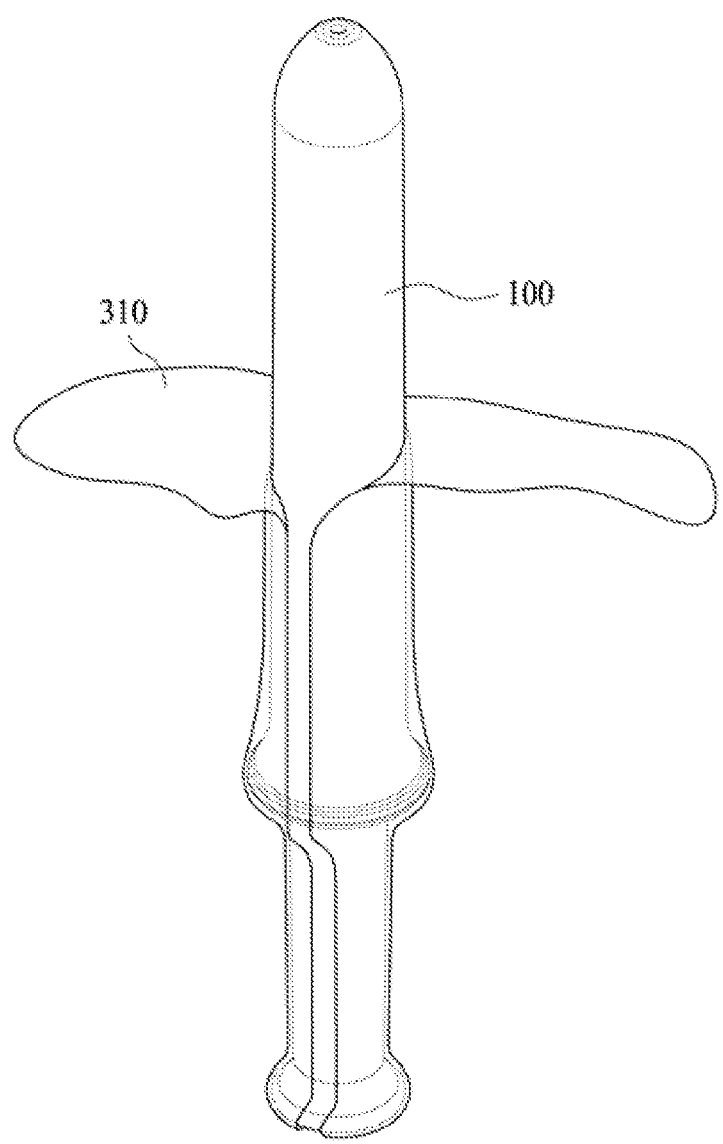

FUNCTIONAL DRUG INJECTION MODULE

CROSS-REFERENCE TO RELATED APPLICATION

This application claims under 35 U.S.C. § 119(a) the benefit of Korean Patent Application No. 10-2021-0107140 filed on Aug. 13, 2021, the entire contents of which are incorporated herein by reference.

BACKGROUND

(a) Technical Field

The present invention relates to a functional drug injection module, more particularly, to a functional drug injection module that can be easily used by simply unsealing an injection unit, which has a functional solution therein, and opening an outlet.

(b) Background Art

In general, various liquids are often injected into a human body for various purposes recently.

For example, various drug solutions are used, including a washing liquid that is injected into a sexual organ for washing the female sexual organ, a contraceptive liquid that is injected for contraception, drug liquids that are injected for treating hemorrhoids, a venereal disease, etc., or a lubricant that is injected for having sex.

The inside of the sexual organ, the anus, etc. of a human body is a part, where mucous membranes are exposed, and is very sensitive to external stimulation, so the mucous membranes are easily hurt or contaminated. Accordingly, it is required to pay particular attention to inject various liquids described above.

Devices that can inject a liquid into a human body were designed to solve the inconvenience of directly manually injecting a liquid in the related art. Such liquid injection devices are manufactured as disposable products due to sanitary problems and difficulty in washing in most cases, so they are sold with a liquid preaccommodated therein.

However, since a user has to insert the devices into a human body in order to inject a liquid into the human body, maintaining of sealing is important, and particularly, it is required to maximally prevent leakage or contamination of a liquid.

In order to solve these problems, devices for injecting a liquid have been manufactured in the type that prevents leakage through an outlet of the devices using a cover unit, a cap, etc., and additionally seals the devices using a package, a shock-absorber, etc.

However, when a liquid injection device is sealed through several steps in this way, it may cause inconvenience of removing the seals through several steps to use the device and there is a technology for removing such inconvenience.

Therefore, there is a need for a new plan that can solve this problem.

SUMMARY OF THE INVENTION

In order to solve the problems described above, an object of the present invention is to provide a functional drug injection module that enables an injection unit to be used by simply removing at a time a sealing unit that is a package sealing the injection unit and a cover unit that is provided separately from the sealing unit to close an outlet.

The objects to implement in the present invention are not limited to the technical problems described above and other objects that are not stated herein will be clearly understood by those skilled in the art from the following specifications.

In order to achieve the objects of the present invention, a functional drug injection module includes: an injection unit including a body that is elongated, keeps a functional drug therein, has the outlet formed at a front end thereof, and is open at a rear end thereof, and a piston that is inserted in the body through the rear end of the body and discharges the functional drug by longitudinally sliding; a cover unit at least partially formed like a projection, inserted in the outlet, and adjust opening/closing of the outlet by selectively separating; and a sealing unit surrounding the injection unit and the cover unit, having a first crease formed in a longitudinal direction of the injection unit, and separating from the injection unit together with the cover unit by being divided along the first crease by external force.

The sealing unit may be partially integrally formed with or bonded to the cover unit and may also be cut when the cover unit is separated from the injection unit.

In addition, the sealing unit may have: a sealing section elongated in a longitudinal direction of the injection unit and surrounding an outer surface of the injection unit; and a cutting section elongated in a longitudinal direction of the sealing section, being able to be divided by the first crease, and having a longitudinal end coupled to the cover unit.

Further, the sealing unit may further have a separating section configured to surround the cover unit at the longitudinal end of the cutting section and having a second crease at least at a portion along a circumference of the outlet to be also separated when the cover unit is separated.

The separating section may be integrated with the cutting section and may be separated from the sealing section along the first crease and the second crease.

The cutting section may have a corresponding length along the longitudinal direction of the sealing section and may be separated from the sealing section.

In addition, the cutting section may further have an assistant separation member elongated in the longitudinal direction of the injection unit, disposed adjacent to the first crease between the cutting section and the injection unit, and having an end coupled to the cover unit.

According to the functional drug injection module according to the present invention, there is an advantage that the outlet is opened by separating the cover unit from the sealed injection unit without a specific structure and the sealing section is separated by removing the cutting section of the sealing unit, whereby it is possible to unseal the injection unit and simply use the injection unit.

The effects of the present invention are not limited to those described above and other effects not stated herein may be made apparent to those skilled in the art from claims.

BRIEF DESCRIPTION OF THE DRAWINGS

The above and other objectives, features and other advantages of the present invention will be more clearly understood from the following detailed description when taken in conjunction with the accompanying drawings, in which:

FIG. 1 is a view schematically showing the configuration of a functional drug injection module according to the present invention;

FIG. 2 is a side view showing a detailed configuration of the functional drug injection module according to the present invention;

FIG. 3 is a view showing the shape of a sealing unit of the functional drug injection module shown in FIG. 1;

FIG. 4 is a view showing the state in which a cover unit is separated from the functional drug injection module shown in FIG. 1;

FIG. 5 is a view showing the state in which a cutting section shown in FIG. 4 is separated along a crease; and FIG. 6 is a view showing the state in which the cutting section and the sealing section shown in FIG. 5 are completely separated and removed.

DETAILED DESCRIPTION

Hereinafter, embodiments of the present invention will be described in detail with reference to the accompanying drawings. However, in the following description of the present invention, well-known functions or configurations will not be described to make the spirit of the present invention clear.

Further, in the following description of the present invention, terms indicating directions, such as 'front', 'rear', 'up', and 'down', define relative directions so that those skilled in the art can clearly understand the present invention, and the right range of the present invention is not limited thereto.

First, the configuration of a functional drug injection module according to the present invention is described with reference to FIGS. 1 to 3.

FIG. 1 is a view schematically showing the configuration of a functional drug injection module according to the present invention, FIG. 2 is a side view showing a detailed configuration of the functional drug injection module according to the present invention, and FIG. 3 is a view showing the shape of a sealing unit 300 of the functional drug injection module shown in FIG. 1.

As shown in the figures, a functional drug injection module according to the present invention, in a broad meaning, includes an injection unit 100, a cover unit 200, and a sealing unit 300.

The injection unit 100, which is a common syringe type, is filled with a functional drug and can be operated by a user to selectively discharge the functional drug.

In detail, the injection unit 100 has a space, which is elongated and can be filled with a functional drug, and has an outlet 112 formed at the front end to discharge the functional drug. In this embodiment, the injection unit 100, in a broad meaning, includes a body 110 and a piston 120. The functional drug is a liquid that is injected into the body of a user, and generally may be a lubricant, a cleansing agent, a liquid drug, or the like to be harmless to the human body.

The body 110 is elongated to be able to be inserted into a human body and has a space therein that can keep a liquid. The outlet 112 is formed at the front end of the body 110 so that a liquid kept therein can be sprayed, and the rear end of the body 110 is open so that a piston 120 is inserted.

In this embodiment, the body 110 is elongated in the front-rear direction entirely in a curved shape and the transverse cross-section thereof is a circle. Accordingly, when the body is inserted into the user's body, it does not cause a pain. The rear end of the body 110 is formed such that the transverse cross-section gradually increases, so the piston 120 can be easily inserted.

Here, the body 110 according to the present invention is elongated and has the outlet 112 at the front, and a functional drug kept therein is discharged through the outlet 112.

Meanwhile, the piston 120 is inserted through the open rear end of the body 110 to be movable forward and backward. That is, when the piston 120 is inserted in the body 110 and moved forward, the functional drug in the body 110 is pushed to be sprayed through the outlet 112.

In this embodiment, though not shown in the figures, a separate sealing member (not shown) is disposed at the front end of the piston 120, so the sealing member can be pushed forward when the piston 120 is moved forward.

Accordingly, the front end portion of the piston 120 is inserted through the rear end of the body 110, and as the piston 120 longitudinally slides, it can press and discharge the functional drug.

As described above, the injection unit 100 according to the present invention is formed in the shape of a syringe in which the body 110 and the piston 120 are combined, and can selectively discharge the functional drug kept in the accommodation space through the outlet 112 formed at the front end.

The cover unit 200, which surrounds at least a portion of the injection unit 100 and surrounds the outlet 112 at the front, partially protrudes and is inserted in the outlet 112.

In detail, the cover unit 200 partially protrudes like a projection, so the protruding portion corresponds to the size of the outlet 112 and is selectively inserted, thereby adjusting opening/closing. In this embodiment, the cover unit 200 has an outer diameter corresponding to the size of the outlet 112 and protrudes with a predetermined length.

Meanwhile, the sealing unit 300 according to the present invention surrounds and isolates the injection unit 100 and the cover unit 200 from the outside, thereby preventing contamination of the injection unit 100. Further, the sealing unit 300 is configured to be able to be separated by a user.

In detail, the sealing unit 300 surrounds the injection unit 100 and the cover unit 200, has a first crease 322 formed in the longitudinal direction of the injection unit 100, and is divided along the first crease 322 by external force, whereby it is separated from the injection unit 100 together with the cover unit 200. The sealing unit 300 is at least partially integrally formed with or bonded to the cover unit 200, so when the cover unit 200 is separated from the injection unit 100, the corresponding portion is partially cut.

The sealing unit 300 according to the present invention, in a broad meaning, has a sealing section 310, a cutting section 320, and a separating section 330. The sealing section 320 is elongated in the longitudinal direction of the injection unit 100 and surrounds the outer surface including the cylinder and the piston, thereby sealing the injection unit 100 to isolate the injection unit 100 from the outside.

In detail, the sealing unit 300 is made of a transparent or an opaque material in a thin vinyl or wrap type to surround the circumference of the injection unit 100. The sealing unit 300 is provided at both sides of the cutting section 320 vertically elongated, thereby surrounding the cutting section 320 and the injection unit 100.

The cutting section 320 is elongated in the longitudinal direction of the sealing section 310 to be able to be divided by the first crease 322 and is integrated with the sealing section 310. The cutting section 320 is elongated in the longitudinal direction of the injection unit 100 and a longitudinal end thereof is coupled to the cover unit 200.

In detail, the cutting section 320 is elongated and integrated with the sealing section 310 in the shape of a tape vertically crossing the sealing unit 300, and can be selectively separated from the sealing section 310 by external force and can separate a portion of the sealing unit 300 circumferentially surrounding the injection unit 100.

The cutting section 320 has a corresponding length in the longitudinal direction of the sealing section 310, and the sealing section 310 is formed in a disconnected cylindrical shape and the cutting section 320 is disposed at the corresponding portion to surround the injection unit 100 in a complete cylindrical shape.

In the present invention, the cutting section 320 is elongated with a predetermined width such that both width-directional sides are integrally connected with the sealing section 310 to make a cylindrical shape, thereby surrounding the injection unit 100 together. The cutting section 320 is integrated with the sealing section 320 and has the first crease 322 forming the boundary, so the cutting section 320 can be divided from the sealing section 310 by the first crease 322.

That is, the cutting section 320 is integrated with the sealing section 310 to surround the injection unit 100 together and is separated from the sealing section 310 along the first crease 322 by external force from a user, thereby cutting the sealing section 310 to be able to be separated from the injection unit 100.

Here, the cutting section 320 is elongated with a length corresponding to the length of the injection unit 100 and is included together in the portion of the sealing section 310 surrounding the circumference of the injection unit 100. As the cutting section 320 is separated from the sealing section 310, a partial region is removed in the circumferential direction of the injection unit 100.

Accordingly, since the cutting section 320 has a length corresponding to the sealing section 310, when the cutting section 320 is removed, the sealing section 310 can be separated in a completely disconnected cylindrical shape.

Further, the upper end of the cutting section 320 is integrally coupled to the cover unit 200, as shown in the figures, whereby the cover unit 200 is separated from the injection unit 100 and the corresponding portion is also separated from the sealing section 310 so that a user can easily hold the module.

That is, the cutting section 320 is integrated with the cover unit 200 or partially bonded thereto at an end, so when the cover unit 200 is separated from the injection unit 100, the cutting section 320 is partially cut and only a portion thereof is separated from the sealing section 310.

Meanwhile, the separating section 330 surrounds the cover unit 200 at an end portion in the longitudinal direction of the cutting section 320 and has a second crease 324 at least at a portion along the circumference of the outlet 112 to make a boundary with respect to the sealing section 310.

In detail, the separating section 330 is integrated with the sealing section 310 and is divided by the second crease 324 at the end of the portion adjacent to the cover unit 200, so when the cover unit 200 is separated, the separating section 330 is cut along the second crease 324, thereby being separated from the sealing section 310.

Here, the separating section 330 is integrally made of the same as the sealing section 310 and the cutting section 320, and is divided by the second cutting section 320. In this case, the cutting section 320 may be integrated with the separating section 330 at an end and can keep coupled to the cutting section 320 even though it is separated from the sealing section 310 along the second cutting section 320.

In this embodiment, the separating section 330 is bonded to the cutting section 320, but they may be integrated not to separate from each other.

As described above, the sealing unit 300 has the sealing section 310, the cutting section 320, and the separating section 330, which are integrally connected to each other and surround the cover unit 200 and the injection unit 100 to keep them sealed in the initial state. When the separating section 330 and the cutting section 320 are cut and separated from the sealing section 310, the sealing state is removed.

Meanwhile, the cutting section 320 further includes a separate assistant separation member 326 to increase durability of the cutting section 320 and to be able to be stably separated from the sealing section 310.

In detail, the assistant separation member 326 is elongated in the longitudinal direction of the injection unit 100, is disposed adjacent to the first crease 322 between the injection unit 100 and the cutting section 320, and is coupled at an end to the cover unit 200.

The assistant separation member 326 is configured as a separate tape type, is disposed on the rear surface of the cutting section 320, and positioned the first creases 322 to be able to be separated when the cutting section 320 is separated.

In this case, it is preferable that the assistant separation member 326 is made of a material having higher durability than the cutting section 320 and is formed to be the same or relatively long with an end coupled to the separating section 330 or the cover unit 200.

In this embodiment, the assistant separation member 326 has the same length as the cutting section 320 and a relatively small width, and is bonded to the rear surface of the cutting section 320.

Accordingly, when the cutting section 320 and the sealing section 310 are separated, the assistant separation member 326 is also separated together with the cutting section 320, whereby it is possible to prevent the cutting section 320 from being cut at the middle portion.

As described above, the functional drug injection module according to the present invention includes the injection unit 100, the cover unit 200, and the sealing unit 300, and a user can unseal the injection unit 100 by simultaneously removing the cutting section 320 and the separating section 330 from the cover unit 200 with the injection unit 100 and the cover unit 200 sealed by the sealing unit 300.

Next, the state in which the sealing unit 300 according to the present invention is removed is described with reference to FIGS. 4 to 6.

First, as shown in FIG. 4, a user separates the cover unit 200 by applying external force while gripping the cover unit 200 together with the separating section 330 using external force. In this process, the separating section 330 is separated from the sealing section 310 along the second crease 324 and the cover unit 200 is positioned in the separating section 330.

When the separating section 330 is removed from the sealing section 310, the cutting section 320 independently keeps connected with the separating section 330.

Further, as shown in FIG. 5, when the user separates the cutting section 320 from the sealing section 310 along the first crease 322 by pulling the cutting section 320 while gripping the separating section 330. In this process, a longitudinal end of the cutting section 320 is connected with the separating section 330 and the cutting section 320 can be longitudinally separated from the sealing section 310 at the corresponding portion.

Thereafter, as shown in FIG. 6, the sealing section 310 and the cutting section 320 are completely separated, so a partial region surrounding the circumference of the injection unit 100 is removed, whereby the sealing section 310 is simply separated from the injection unit 100.

That is, when the sealing section 310 and the cutting section 320 keep integrally coupled, it is difficult to separate the sealing unit 300 because the sealing unit 300 surrounds the injection unit 100 in a complete cylindrical shape.

However, since the cutting section 320 is removed across the longitudinal direction of the injection unit 100, it is possible to use the injection unit 100 after removing the sealing section 310.

As described above, the sealing unit 300 is sealed in close contact with the functional drug injection module according to the present invention to prevent contamination. Further, a user can easily use the injection unit 100 by simply removing the sealing unit 300.

Although specific embodiments of the present invention were described above, the present invention is not limited to the embodiments and it is apparent to those skilled in the art that the present invention may be changed and modified in various ways without departing from the spirit and scope of the present invention. Accordingly, the changes and modifications should not be construed individually from the spirit and scope of the present invention and should be construed as being included in claims.

What is claimed is:

1. A functional drug injection module comprising:
    an injection unit including a body that is elongated, keeps a functional drug therein, has an outlet formed at a front end thereof, and is open at a rear end thereof, and a piston that is inserted in the body through the rear end of the body and discharges the functional drug by longitudinally sliding;
    a cover unit at least partially formed in the shape of a projection, inserted in the outlet, and capable of closing the outlet by inserting the cover unit in the outlet and capable of opening the outlet by separating the cover unit from the outlet; and
    a sealing unit at least partially surrounding the injection unit and the cover unit, having a first crease formed in a longitudinal direction of the injection unit, and separating from the injection unit together with the cover unit by being divided along the first crease by external force,
    wherein the sealing unit comprises:
    a sealing section elongated in a longitudinal direction of the injection unit and surrounding an outer surface of the injection unit; and
    a cutting section elongated in a longitudinal direction of the sealing section, being able to be divided by the first crease, and having a longitudinal end coupled to the cover unit.

2. The functional drug injection module of claim 1, wherein the sealing unit is partially formed integrally with or bonded to the cover unit and is cut when the cover unit is separated from the injection unit.

3. The functional drug injection module of claim 1, wherein the sealing unit further comprises a separating section configured to surround the cover unit at the longitudinal end of the cutting section and having a second crease at least at a portion along a circumference of the outlet to be also separated when the cover unit is separated.

4. The functional drug injection module of claim 3, wherein the separating section is integrated with the cutting section and is separated from the sealing section along the first crease and the second crease.

5. The functional drug injection module of claim 3, wherein the cutting section has a corresponding length along the longitudinal direction of the sealing section and can be separated from the sealing section.

6. The functional drug injection module of claim 3, wherein the cutting section further has an assistant separation member elongated in the longitudinal direction of the injection unit, disposed adjacent to the first crease between the cutting section and the injection unit, and having an end coupled to the cover unit.

* * * * *